United States Patent
Chang et al.

(10) Patent No.: US 8,168,813 B2
(45) Date of Patent: May 1, 2012

(54) POROUS ORGANIC-INORGANIC HYBRID MATERIALS AND ADSORBENT COMPRISING THE SAME

(75) Inventors: Jong-San Chang, Daejeon (KR); Young Kyu Hwang, Daejeon (KR); Sung Hwa Jhung, Daejeon (KR); Do-Young Hong, Gyeonggi-do (KR); You-Kyung Seo, Busan (KR)

(73) Assignee: Korea Research Institue of Chemical Technology, Daejeon (KR)

( * ) Notice: Subject to any disclaimer, the term of this patent is extended or adjusted under 35 U.S.C. 154(b) by 413 days.

(21) Appl. No.: 12/484,090

(22) Filed: Jun. 12, 2009

(65) Prior Publication Data

US 2009/0263621 A1  Oct. 22, 2009

Related U.S. Application Data

(63) Continuation-in-part of application No. PCT/KR2007/006472, filed on Dec. 12, 2007.

(30) Foreign Application Priority Data

Dec. 13, 2006 (KR) .......... 10-2006-0127343
Jul. 26, 2007 (KR) .......... 10-2007-0075205
Aug. 1, 2007 (KR) .......... 10-2007-0077335

(51) Int. Cl.
*C07F 15/00* (2006.01)
*B32B 3/12* (2006.01)
(52) U.S. Cl. .......... 556/138; 428/116; 428/304.4; 428/402; 556/147
(58) Field of Classification Search .......... 556/138, 556/147; 428/116, 304.4, 402
See application file for complete search history.

(56) References Cited

U.S. PATENT DOCUMENTS

| | | | |
|---|---|---|---|
| 5,298,179 A | 3/1994 | Ukita et al. | |
| 6,675,601 B2 | 1/2004 | Ebara | |
| 6,959,875 B2 | 11/2005 | Yabu et al. | |
| 6,978,635 B2 | 12/2005 | Yabu et al. | |
| 2006/0074160 A1 | 4/2006 | Handa et al. | |
| 2007/0239124 A1 | 10/2007 | Handa et al. | |
| 2011/0118490 A1* | 5/2011 | Hwang et al. | 556/44 |

FOREIGN PATENT DOCUMENTS

| | | |
|---|---|---|
| JP | 04-066125 A | 3/1992 |
| JP | 06-180062 A | 6/1994 |
| JP | 16-210924 A | 7/2004 |
| KR | 2006-0122576 A | 11/2006 |
| KR | 100680767 B1 | 2/2007 |
| KR | 100803964 B1 | 2/2008 |
| KR | 20090011999 A | 2/2009 |
| WO | WO 2004/003036 A | 1/2004 |

OTHER PUBLICATIONS

PCT International Search Report for PCT/KR2007/006472, Mailing date Mar. 20, 2008, 3 pages.
PCT Written Opinion of the International Searching Authority for PCT/KR2007/006472, Mailing date Mar. 20, 2008, 5 pages.
Office Action issued in corresponding Korean Patent Application No. 2006-0127343, dated Sep. 20, 2007.
Office Action issued in corresponding Korean Patent Application No. 2007-0077335, dated Nov. 12, 2008.
S. Kitagawa et al., "Functional Porous Coordination Polymers", *Angew. Chem. Intl. Ed.*; 2004, 43, 2334-2375.
S.L. James, "Metal-organic frameworks", *Chem. Soc. Rev.*, 2003, 32, 276-288.
M.J. Rosseinsky, "Recent developments in metal-organic framework chemistry: design, discovery, permanent porosity and flexibility", *Microporous Mesoporous Materials*, 2004, 73, 15-30.
G. Férey et al., "Crystallized Frameworks with Giant Pores: Are There Limits to the Possible?" *Accounts of Chemical Research*, 2005, 38, 217-225.
S.H. Jhung et al., "Microwave Synthesis of a Nanoporous Hybrid Material, Chromium Trimesate", *Bulletin of Korean Chemical Society*, 2005, 26, 880-881.
G. Férey et al., "A Chromium Terephthalate—Based Solid with Unusually Large Pore Volumes and Surface Area", *Science*, 2005, 309, 2040-2042.

* cited by examiner

*Primary Examiner* — Porfirio Nazario Gonzalez
(74) *Attorney, Agent, or Firm* — SNR Denton US LLP

(57) ABSTRACT

The present invention relates to an adsorbent using the porous organic-inorganic hybrid material(s) containing iron having a large surface area and a high pore volume, in particular, a water adsorbent. Also, it relates to an adsorbent that can be used in humidifiers, dehumidifiers, coolers/heaters, a refrigerating machine or an air conditioner, etc., which can easily absorb or desorb at 100° C. and below, and has a great adsorption amount per weight of the adsorbent.

Also, the present invention relates to a novel preparation method of porous organic-inorganic hybrid material(s), in particular, a preparation method characterized by not using hydrofluoric acid, porous organic-inorganic hybrid material(s) prepared by said preparation method, and a use as an adsorbent thereof.

27 Claims, 6 Drawing Sheets

[Fig. 1]
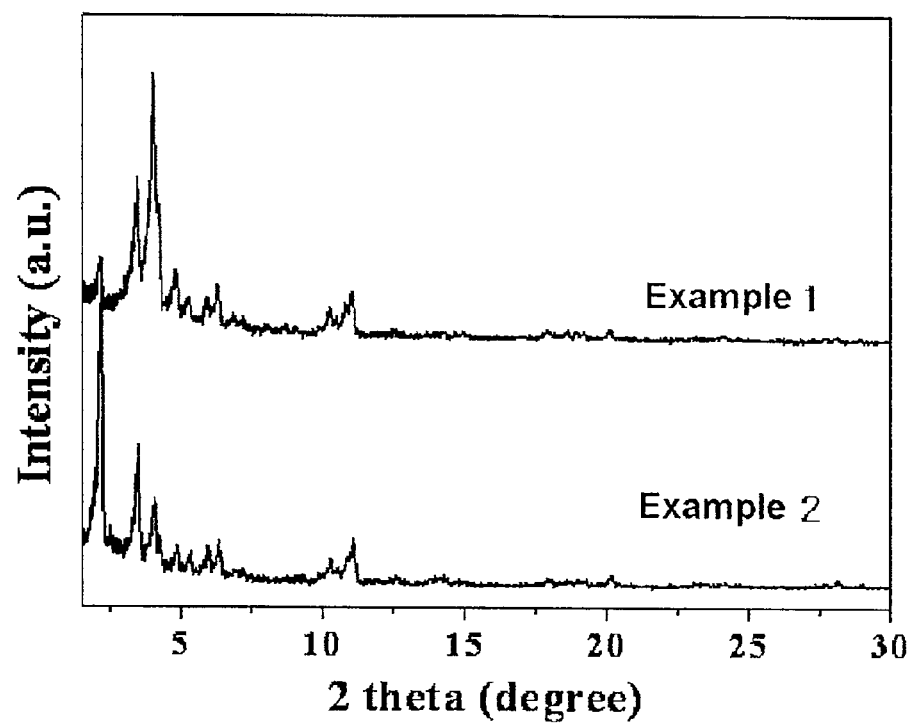
[Fig. 2]
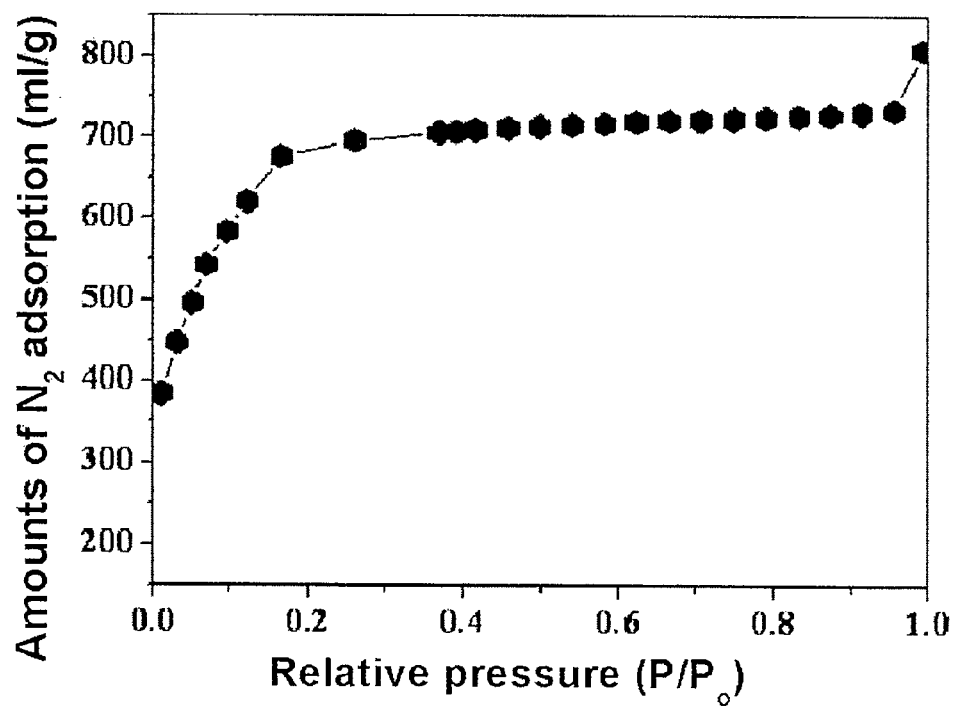

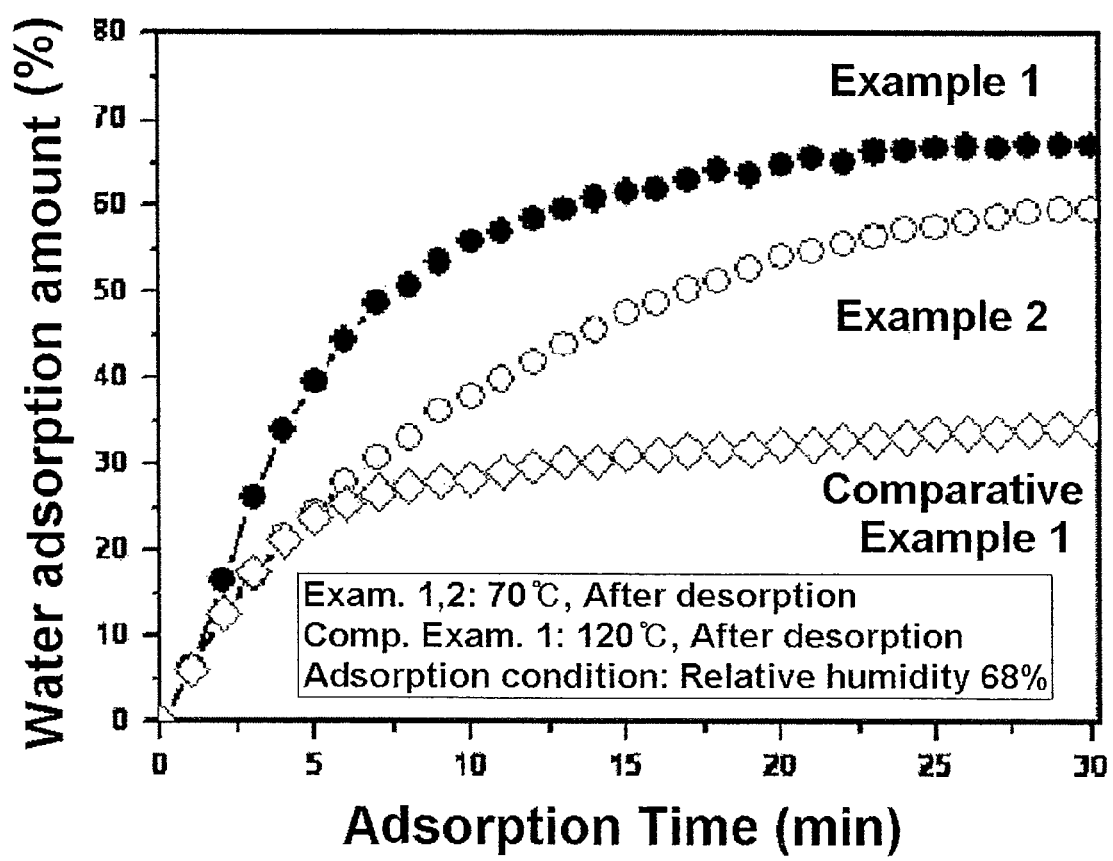
[Fig. 3]

[Fig. 4]
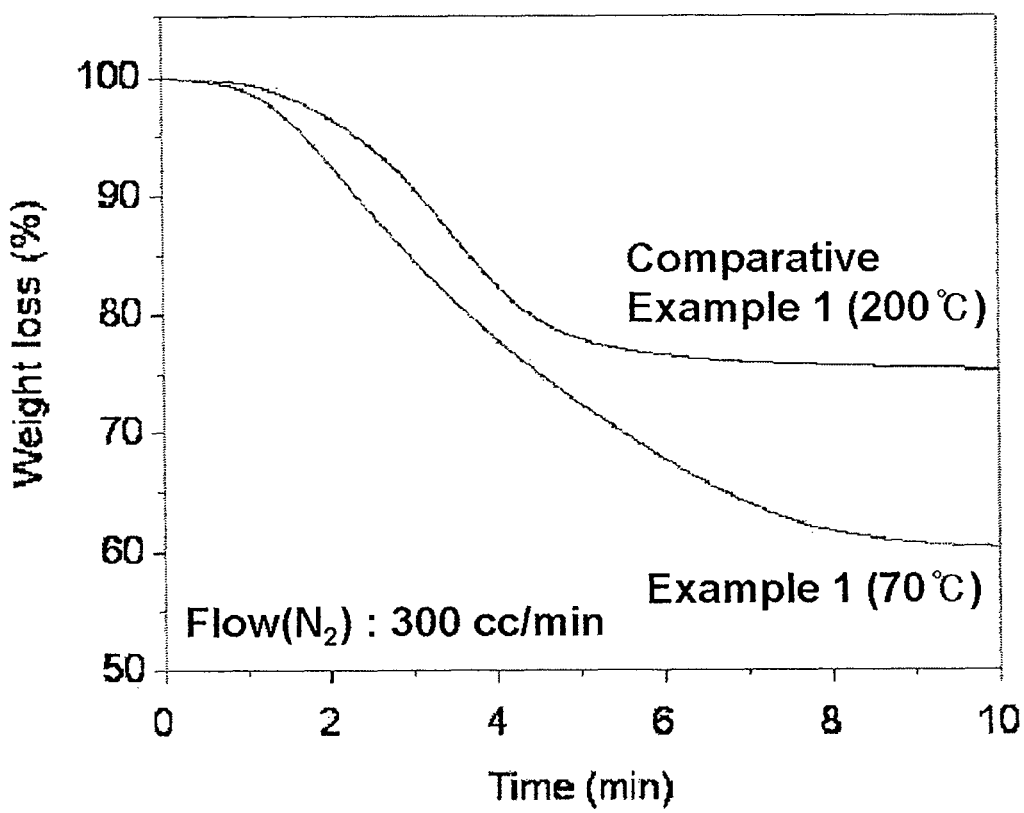
[Fig. 5]
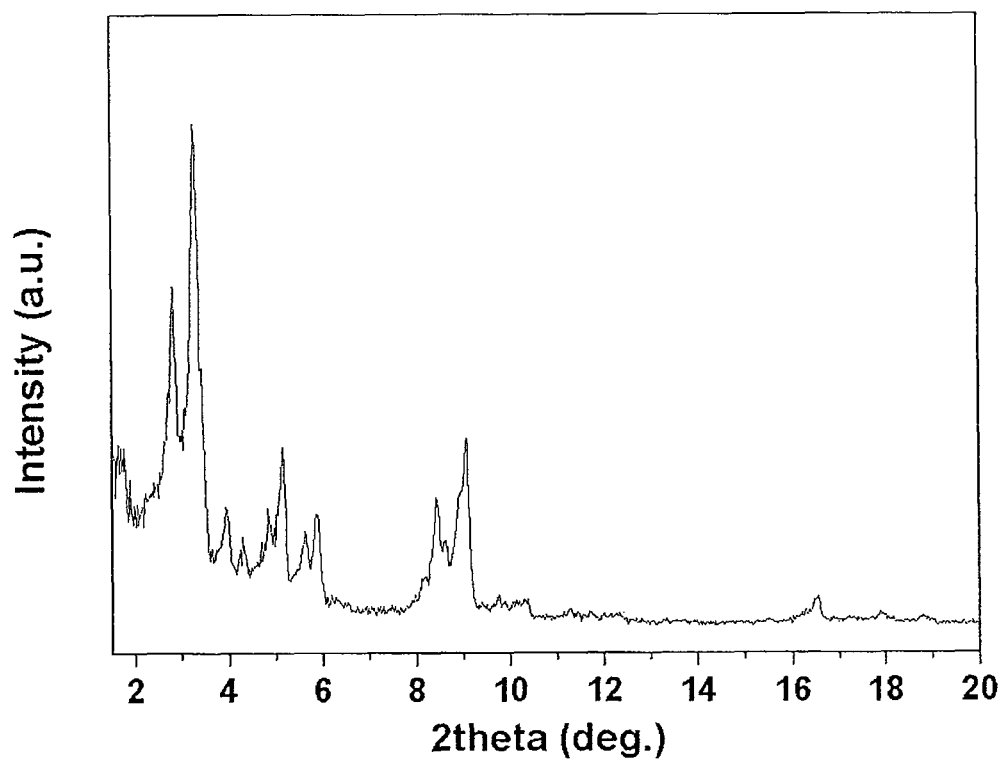

[Fig. 6]
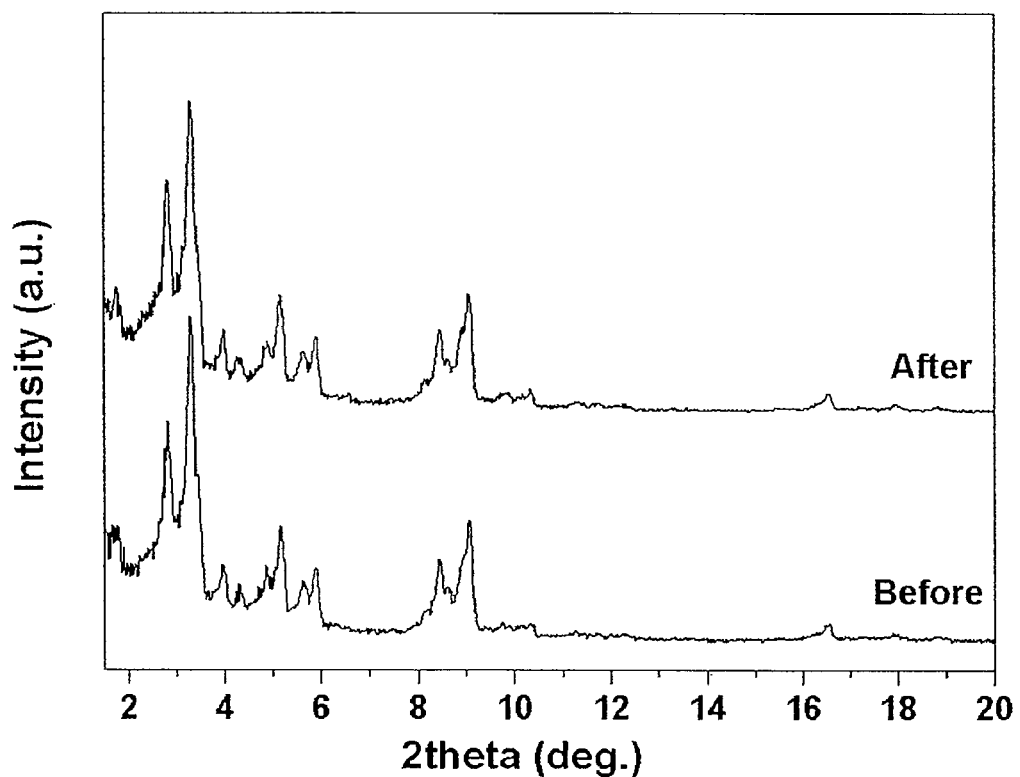
[Fig. 7]
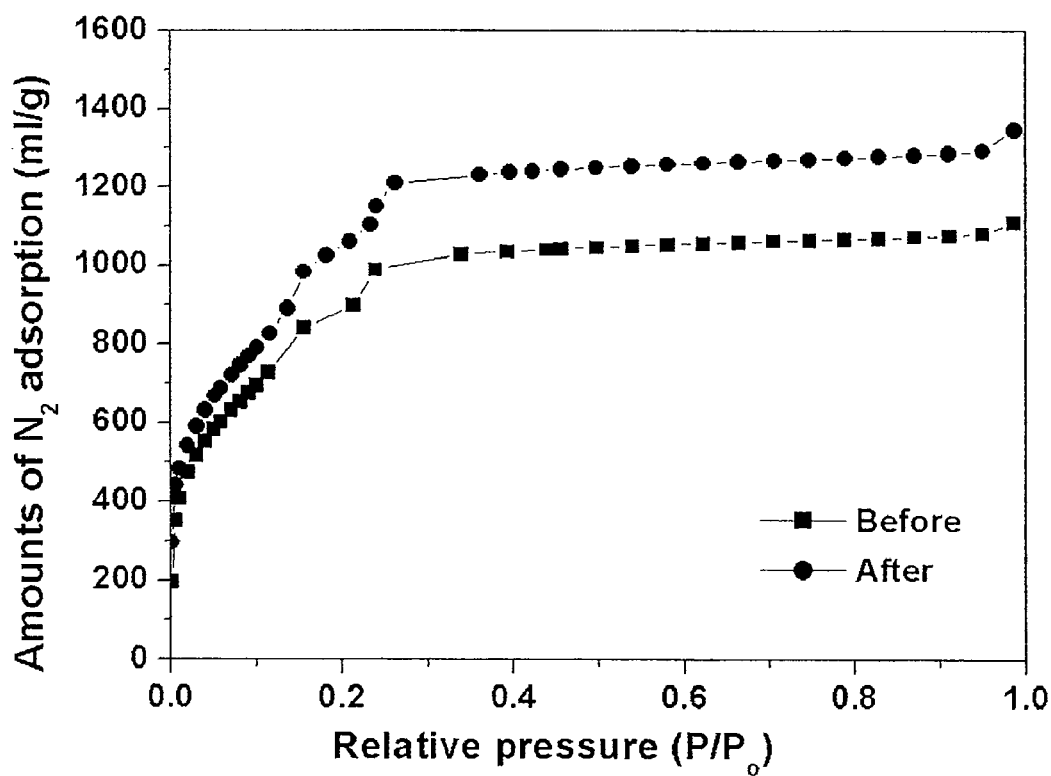

[Fig. 8]
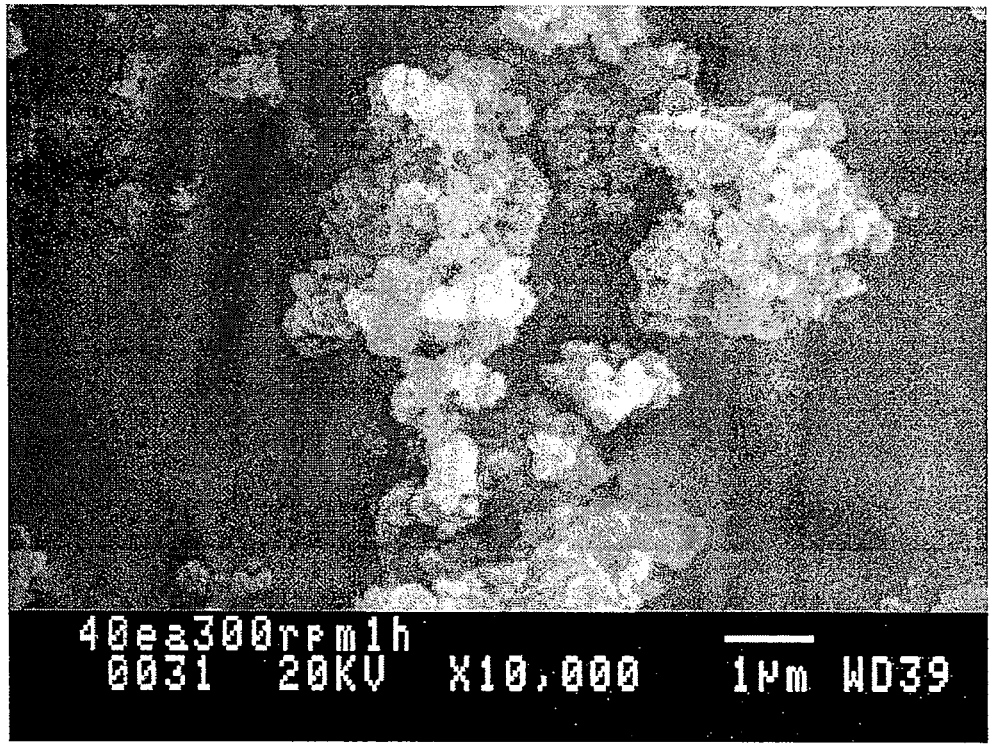
(a)
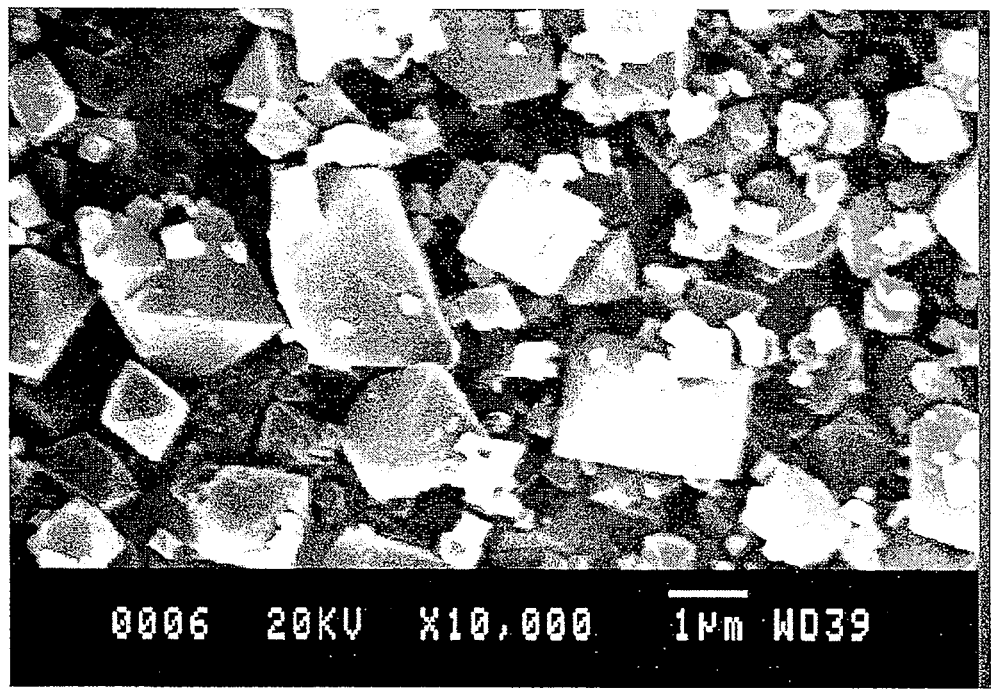
(b)

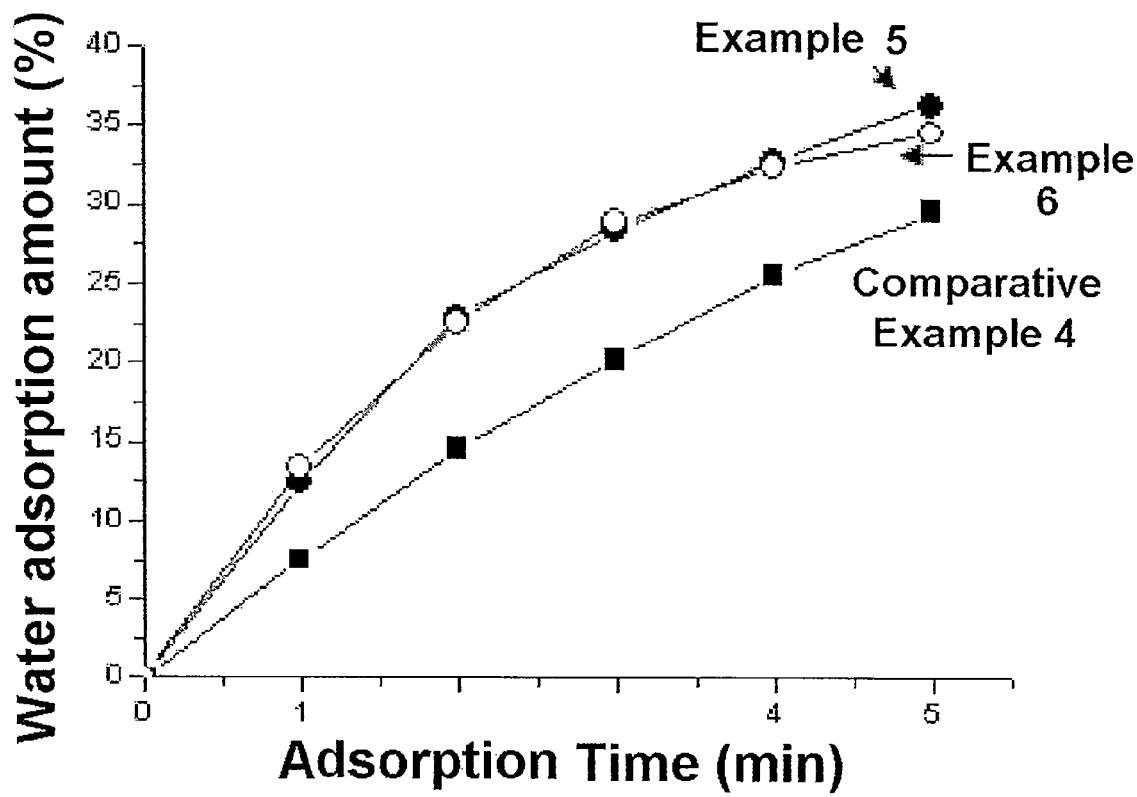
[Fig. 9]

POROUS ORGANIC-INORGANIC HYBRID MATERIALS AND ADSORBENT COMPRISING THE SAME

CROSS-REFERENCE TO RELATED APPLICATIONS

This is a continuation-in-part of prior International Patent Application No. PCT/KR2007/006472, filed on Dec. 12, 2007, which claims priority from Korean Patent Application No. 10-2006-0127343, filed on Dec. 13, 2006, Korean Patent Application No. 10-2007-0075205, filed on Jul. 26, 2007 and Korean Patent Application No. 10-2007-0077335, filed on Aug. 1, 2007, each of which is incorporated herein by reference in their entirety.

TECHNICAL FIELD

The present invention relates to a method for preparing porous organic-inorganic hybrid material(s), an adsorbent comprising the same, and the catalytic uses of the organic-inorganic hybrid material(s). More particularly, the present invention relates to an adsorbent that can easily absorb and desorb at a low temperature of 100° C. and below, and has a large difference between the adsorption amount in adsorption condition and the adsorption amount in desorption condition. Also, the present invention relates to an adsorbent using the porous organic-inorganic hybrid material(s) having properties such as nano size pores and large surface area and pore volume.

Also, the present invention relates to a novel method for preparing porous organic-inorganic hybrid material(s) wherein use of hydrofluoric acid has been eliminated, and a novel use as an adsorbent of the porous organic-inorganic hybrid material(s) obtained by said preparation method.

In particular, with regard to the novel use as an adsorbent of the porous organic-inorganic hybrid material(s) according to the present invention, the present invention relates to a water adsorbent that can be used in humidifiers, dehumidifiers and coolers/heaters, which can easily adsorb or desorb at 100° C. and below, and has a great adsorption amount per weight of the adsorbent. Also, the present invention relates to use of the porous organic-inorganic hybrid material(s) of the present invention having a large surface area and uniform porous properties as an adsorbent having excellent adsorption efficiency against specific hazardous materials.

The porous organic-inorganic hybrid material(s) prepared according to the present invention can be defined as porous organic-inorganic polymer compounds formed by binding a central metal ion (e.g., iron ion) with an organic ligand. The compounds are crystalline compounds having a pore structure of a molecular size or nano size and containing both an organic compound and an inorganic compounds within the framework structure.

BACKGROUND ART

The term "porous organic-inorganic hybrid material(s)" has a broad meaning, and in general, it is also referred to as "porous coordination polymers" [Angew. Chem. Intl. Ed., 43, 2334 (2004)], or "metal-organic frameworks" [Chem. Soc. Rev., 32, 276 (2003)].

At present, scientific research is focused on materials developed by integrating molecule coordination bonding with material science. Said material(s) has large surface area and pores of a molecular size or nano size, and thus can be used not only for adsorbents, gas storing materials, sensors, membranes, functional thin films, catalysts and catalyst carriers, etc., but also for including guest molecules smaller than their pore size or separating molecules depending on sizes of the molecules by using their pores. Thus, they have gained much importance.

Porous organic-inorganic hybrid material(s) have been prepared by various methods. Usually, they have been prepared by a hydrothermal synthesis reacting at high temperature by using water as a solvent or by reacting near room temperature by using solvent diffusion, or a solvothermal synthesis using an organic solvent [Microporous Mesoporous Mater., 73, 15 (2004); Accounts of Chemical Research, 38, 217 (2005)].

Porous organic-inorganic hybrid material(s) have been recognized to have unique features that they can be used not only for catalysts, catalyst carriers, adsorbents, ion exchanging materials and gas storing materials, but also for storing, preparing and separating nanomaterials, and for nanoreactors, due to their characteristics such as large surface area, crystalline structure of a very high regularity and relatively high thermal stability, etc. In this regard, Cr-MIL-100, which is an organic-inorganic hybrid material(s) of MIL-100 structure (MIL: Materials of Institute Lavoisier), has been reported [Bulletin of Korean Chemical Society vol. 26, p. 880 (2005)].

However, as for the organic-inorganic hybrid material(s) containing Cr as stated above, due to the Cr component that is harmful to the human body, its use is relatively limited. In particular, iron-organic-inorganic hybrid material(s) having Fe as a central metal which is not harmful to the human body cannot be easily formed by the synthetic method of the organic-inorganic hybrid material(s) containing the Cr component, and thus development of a novel preparation method for said materials has been needed.

Also, as for the synthesis of porous organic-inorganic hybrid material(s) by hydrothermal synthesis, in general, a mixed-acid comprising nitric acid, hydrofluoric acid, etc. is used in order to regulate the rate of forming crystals. As for representative porous organic-inorganic hybrid material(s) prepared by the hydrothermal synthesis, MIL-100 (Cr) represented by formula of $Cr_3O(H_2O)_2F[C_6H_3—(CO_2)_3]_2 \cdot nH_2O$ (n~14.5) and MIL-101 (Cr) represented by formula of $Cr_3F(H_2O)_2O[C_6H_4(CO_2)_2]_3 \cdot nH_2O$ (n~25) have been reported [Science 23, 2040 (2005); Accounts of Chemical Research, 38, 217 (2005)]. The organic-inorganic hybrid material(s) of a metal-organic framework structure where the Cr component is substituted by another metal have not been reported yet.

Meanwhile, an adsorbent that can easily adsorb and desorb water has various uses. For example, the dehumidifier can utilize the adsorbent having a property of adsorbing water at low temperature and desorbing water when it is heated to high temperature. Also, when an adsorbent is used in coolers/heaters, for heating, the adsorbent can be used instead of the humidifier by adsorbing the outdoor moisture at low temperature and introducing the moisture to the indoors to desorb in the indoors at high temperature, and for cooling, a comfortable indoors atmosphere can be obtained by adsorbing the indoor moisture at low temperature and desorbing the moisture in the outdoors at high temperature to send it to the outdoors. Air-conditioners and humidity controllers applying such concept were suggested in U.S. Pat. Nos. 6,978,635, 6,959,875, 6,675,601, etc. However, the patents do not mention on the adsorbent used in such devices in detail, but only mention that silica gel, zeolite, ion exchange resin are used, or that an adsorbent is used. Also, such adsorbent not only has a low adsorption amount, but also causes the operation cost to rise by requiring a high temperature of at least 100° C. even for desorption.

Therefore, it is necessary to develop an adsorbent that can desorb at low temperature and has a large difference between adsorption amount and desorption amount. However, there were always problems such that if the adsorption amount increases, it is difficult to desorb, and in case the adsorption amount is low, the difference between the adsorption amount and the desorption amount is not great.

Also, until now, active carbon and hydrophobic zeolite were mainly used as adsorbents that can remove specific hazardous materials of vapor phase or particulate phase comprising volatile organic compounds (VOCs). Active carbon has lots of nano pores, and thus has a very large surface area, and a strong adsorption strength against non-polar molecules, and thus has an excellent effect in removing exhaust gas, removing smell and decoloring, whereas zeolite is a hydrophilic adsorbent having a pore diameter of about 3~10? and thus has a strong adsorption property to carbon monoxide, carbon dioxide and water. However, most adsorbents only have hydrophobic properties, and thus have disadvantages that they cannot effectively adsorb and remove volatile organic compounds containing water.

DISCLOSURE OF INVENTION

Technical Problem

Accordingly, the first embodiment of the present invention provides an adsorbent that has a high water adsorption amount and that can easily desorb at a relatively low temperature of 100° C. and below, for example at 60~80° C., and an adsorbent having excellent adsorption amount and adsorption property by using the porous organic-inorganic hybrid material(s) containing iron.

Therefore, it is an object of the present invention to provide a water adsorbent that has a high water adsorption amount and that can easily desorb at a relatively low temperature.

More particularly, it is an object of the present invention to provide a water adsorbent using porous organic-inorganic hybrid material(s) containing iron having a large surface area and a large pore volume as a substance that has a high water adsorption amount and that can easily desorb at a relatively low temperature.

Also, it is another object of the present invention to provide a method for preparing porous organic-inorganic hybrid material(s) containing iron having a large surface area and a large pore volume.

An iron precursor containing the environmental friendly Fe instead of Cr as the metal component contained in the conventional porous organic-inorganic hybrid material(s) is reacted with an organic ligand. In case of performing the crystallization by heating the mixture with a solvent in the presence of a mixed-acid comprising nitric acid and hydrofluoric acid, a porous organic-inorganic hybrid material(s) containing iron having a large surface area and a large pore volume such as a surface area of at least 500 $m^2/g$, or larger than 1,700 $m^2/g$ and a pore volume of at least 0.3 ml/g or larger than 0.8 ml/g is prepared. It has been confirmed that when this is used as a water adsorbent, water can be easily desorbed at a temperature of 100° C. and below, and that the water adsorption amount per weight of the adsorbent is very high, and the present invention was completed accordingly.

The second embodiment of the present invention provides a method for preparing and purifying porous organic-inorganic hybrid material(s) having a relatively small nano particle size through a environmental friendly novel preparation method, wherein hydrofluoric acid is not used at all in some cases when preparing porous organic-inorganic hybrid material(s), and provides the use of porous organic-inorganic hybrid material(s) prepared by said method as an adsorbent. Also, it is an object of the present invention to provide a method for preparing porous organic-inorganic hybrid material(s) through a quick and continuous-type manner by irradiating microwaves. In particular, with regard to the use as an adsorbent, it is an object of the present invention to provide an adsorbent having excellent adsorption efficiency against water, or specific hazardous materials such as VOC, hazardous materials causing a sick house syndrome.

Technical Solution

The first embodiment of the present invention relates to a water adsorbent. In particular, the adsorbent is characterized by using porous organic-inorganic hybrid material(s) containing environmental friendly iron as a metal component.

The present invention provides an adsorbent using porous organic-inorganic hybrid material(s) containing iron that can easily desorb at low temperature and that has a great difference between the adsorption amount at low temperature and the adsorption amount at high temperature. The adsorbent according to the present invention has a surface area of at least 500 $m^2/g$, or larger than 1,700 $m^2/g$ and a pore volume of at least 0.3 ml/g or larger than 0.8 mL/g, and contains both organic and inorganic compounds within the framework structure. Also, the porous organic-inorganic hybrid material(s) containing iron is characterized in that it is prepared by a reaction between an iron precursor and an organic ligand compound that can be coordinated with the iron precursor.

In case the surface area and pore volume are smaller than the above values, it does not have a strong effect as a water adsorbent. Also, it is better if the surface area and pore volume are as large as possible. However, as a range that can be substantially realized in the preparation method, the upper limit of the surface area is about 10,000 $m^2/g$, and the upper limit of the pore volume is about 10 mL/g. The porous organic-inorganic hybrid material(s) containing iron of the present invention has a surface area of 1,700~2,500 $m^2/g$ and a pore volume of 0.8~1.2 mL/g.

Also, as for the conventional adsorbent, the ratio of water adsorption rate at 100° C. against the water adsorption amount at room temperature is 0.5~1. Thus, there is a problem that 50% and less of the water adsorbed is desorbed at a temperature of 100° C. and below, and thus the desorption property is not good at low temperature. However, as for the adsorbent of the present invention, it has a property that at least 80%, more preferably at least 90%, of the water adsorbed is desorbed at a temperature of 100° C. and below. Further, after being dried at 60~80° C. for 10~30 minutes, the water adsorption amount at a relative humidity of 60~80% is 0.2~1.0, or 0.4~0.7 g/g of weight of the adsorbent, and thus the water adsorbent amount per weight of the adsorbent is very high. Therefore, the water adsorbent of the present invention has a very high water adsorption amount. In addition, at a low temperature of 100° C. and below, the adsorbent can easily desorb and has a faster desorption rate than the conventional adsorbent, and thus is suitable to be used to adjust humidity.

In the second embodiment of the present invention, the present invention provides a novel method for efficiently preparing porous organic-inorganic hybrid material(s). In particular, the present invention provides a method for preparing porous organic-inorganic hybrid material(s) having nano size particles wherein use of hydrofluoric acid has been eliminated in the hydrothermal synthesis. Also, said preparation method of the present invention is characterized by comprising a method of purifying in order to increase the surface area of the porous organic-inorganic hybrid material(s). Further, the present invention relates to a novel use characterized by using the porous organic-inorganic hybrid material(s) obtained by the novel preparation method as a water adsorbent, an adsorbent for removing specific hazardous materials such as VOC (volatile organic compounds), etc. Said specific hazardous materials comprise materials in vapor phase or particular phase such as formaldehyde, acetaldehyde, tar, nitrosoamines and polycyclicaromatic hydrocarbons, causing a sick house syndrome in addition to volatile organic compounds. Also, the present invention relates to a novel use characterized by using the porous organic-inorganic hybrid material(s) obtained by the novel preparation method as a water adsorbent, an adsorbent for removing specific hazardous materials in vapor phase or particular phase.

Hereinafter, the present invention is explained in more detail.

With regard to the first embodiment of the present invention, the porous organic-inorganic hybrid material(s) containing iron used as an adsorbent according to the present invention is prepared by a method comprising following steps:

(1) preparing a reaction solution containing a mixture of an iron or iron salt as an iron precursor, an organic ligand, a solvent and a mixed-acid comprising nitric acid and hydrofluoric acid as a reaction accelerant; and (2) heating the reaction solution.

As an organic compound which may be another component contained in a porous organic-inorganic hybrid material(s) and may act as a ligand, referred to as a linker, any organic compound capable of coordination bonding can be used. For example, functional groups that can coordinate can be —$CO_2^-$, —N, carboxylic acid group, anion group of carboxylic acid, amino group (—$NH_2$), imino group

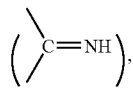

amide group (—$CONH_2$), sulfonic acid group (—$SO_3H$), anion group of sulfonic acid (—$SO_3^-$), methanedithioic acid group (—$CS_2H$), anion group of methanedithioic acid (—$CS_2^-$), pyridine group, pyrazine group, etc.

In order to induce more stable organic-inorganic hybrid material(s), organic compounds having at least two sites for coordination, e.g., being bidentate or tridentate are advantageous. The organic compound may be a neutral organic compound such as bipyridine, pyrazine, etc., anionic organic compounds, e.g., anions of carbonic acid such as terephthalate, naphthalenedicarboxylate, benzenetricarboxylate, glutarate, succinate, etc., and cationic materials, if these have a site for coordination. As for the anions of carbonic acid, in addition to anions having aromatic rings such as terephthalate, any anions, e.g., linear carbonic acid anions such as formate, and anions having non-aromatic rings such as cyclohexyldicarbonate can be used.

Also, in addition to an organic compound having a site for coordination, an organic compound which may be converted to be coordinated in reaction condition due to a potential site for coordination can be used as well. That is, even though organic acids such as terephthalic acid are used, the organic compound such as terephthalate may be bonded to a metal component, after reaction. Representative examples of the organic compounds which can be used include an organic acid or anion thereof selected from benzenedicarboxylic acid, naphthalenedicarboxylic acid, benzenetricarboxylic acid, naphthalenetricarboxylic acid, pyridinedicarboxylic acid, bipyridyldicarboxylic acid, formic acid, oxalic acid, malonic acid, succinic acid, glutaric acid, hexanedioic acid, heptanedioic acid and cyclohexyldicarboxylic acid, pyrazine, bipyridine, etc. Further, one or more organic compounds can be mixed together to be used. It is preferable to use terephthalic acid or benzenetricarboxylic acid.

The method for preparing the porous organic-inorganic hybrid material(s) containing iron, the adsorbent according to the present invention, can be prepared by adding an iron precursor, an organic ligand, a solvent and a mixed-acid comprising hydrofluoric acid and nitric acid as a reaction promoter to the reactor and sealing it, and heating the reactor to 100~250° C. while maintaining the reaction temperature using microwaves or electricity and maintaining the pressure to autogeneous pressure.

As stated above, the method for preparing organic-inorganic hybrid material(s) containing iron according to the present invention is characterized by using acid, preferably, a mixed-acid comprising hydrofluoric acid and nitric acid. In particular, the iron-containing organic-inorganic hybrid material(s) of the present invention show a remarkable improvement in crystallinity and decrease in crystal size in comparison with the conventional synthetic methods which use only hydrofluoric acid. With the conventional preparation method using hydrofluoric acid, organic-inorganic hybrid material(s) containing iron having a surface area larger than 1,700 $m^2/g$ and a pore volume larger than 0.8 mL/g cannot be prepared. Referring to the results of the examples and comparative examples, in case of using the conventional hydrofluoric acid, the BET surface area is 1,590 $m^2/g$ and is remarkably lower than the BET surface area of 2,050 $m^2/g$ using a mixed-acid. Also, the pore volume is 1.0 ml/g in case of using a mixed-acid, whereas the pore volume is 0.7 ml/g and lower in case of using hydrofluoric acid. Also, when a mixed-acid is used, although it has a very short reaction time (within 2 minutes when using microwaves) compared with the case of not using a mixed-acid, it has been confirmed to have an effect such that the crystallinity is improved and the yield is almost the same. However, it is difficult to prepare organic-inorganic hybrid material(s) having sufficient crystallinity even if an acid such as acetic acid, sulfuric acid, etc. as other acid, or salt such as ammonium fluoride and sodium chloride, etc. are used. In the preparation method of the present invention, the desired iron-containing organic-inorganic hybrid material(s) of the present invention can be prepared by using nitric acid and hydrofluoric acid in a molar ratio of 0.1~1:1~0.1 in a mixed-acid. If the molar ratio of nitric acid or hydrofluoric acid deviates from the above range, there are some disadvantages such that the yield is decreased and the reaction time elongated too much.

In addition to a metal component and an organic compound, a suitable solvent is required for preparing porous organic-inorganic hybrid material(s). As said solvent, any substance among water, alcohols, ketones and hydrocarbons can be used, and two or more solvents can be mixed together to be used. Preferably, one or a mixture of at least two selected from water, alcohols having 1~10 carbon atoms such as methanol, ethanol, propanol, ketones having 2~10 carbon atoms such as acetone, methylethylketone, and hydrocarbons having 5~20 carbon atoms such as hexane, heptane, octane can be used. More preferably, water can be used.

Said iron precursor can be mixed with an organic compound in a ratio of 1:0.1~10 (molar ratio). Said ratio can be properly adjusted depending on the kind of the metal component and organic compound. In the present invention, as an iron precursor, iron salt such as nitrogen iron, iron in the form of metal powder, etc. is used, and as an organic ligand, terephthalic acid or benzenetricarboxylic acid is more preferable.

In the present invention, the reaction temperature for preparing porous organic-inorganic hybrid material(s) is not substantially limited. However, a temperature of at least room temperature or at least 100° C. is suitable. A temperature of from room temperature to 250° C., or 100~250° C. is preferable, and a temperature of 150~220° C. is more preferable. If said reaction temperature is too low, the reaction rate is slow and thus not efficient, and if the reaction temperature exceeds 250° C. and thus too high, materials having no pores can be easily obtained and the reaction rate becomes too fast so that impurities can be easily included. Also, the inner pressure of the reactor becomes higher, which makes the constitution of the reactor not economic. Although the reactor pressure is not substantially limited, it is convenient to synthesize the materials at autogeneous pressure of the reaction materials at reaction temperature. Also, the reaction may be performed at high pressure by adding inert gas such as nitrogen, helium. In case microwaves are irradiated as a heat source in said reaction, microwaves of a frequency of about 300 MHz~300 GHz can be used for heating the reaction material. However, microwaves of a frequency of 2.45 GHz, 0.915 GHz, are generally used in industries.

The method irradiating microwaves has a shorter reaction time, a relatively smaller particle size of porous organic-inorganic hybrid material(s), and large surface area value compared with the method using electric heating, and thus has more excellent properties as a water adsorbent.

Also, in order to be used as an adsorbent in humidifiers or dehumidifiers, the adsorption and desorption property within the first 10 minutes, more preferably the first 5 minutes, are important. That is, although the adsorption amount is large, if its rate is too slow, the adsorbent may not be suitable to be used for humidifiers and dehumidifiers. However, as for the adsorbent prepared by the method of irradiating microwaves among the adsorbent according to the present invention, the adsorption rate is very high, and the desorption rate is excellent, and thus the adsorbent has properties more suitable to be used for such use. That is, after being dried at 60~80° C. for 10~30 minutes and kept in a relative humidity of 60~80% for 5 minutes, the water adsorption amount was 0.35~0.45 g/g of weight of the adsorbent, and thus the initial adsorption rate is very high.

In said preparation method, the reaction can be performed by the batch-type reactor and the continuous-type reactor. The batch-type reactor has a low productivity per hour, and thus is suitable for producing a small amount of a porous organic-inorganic hybrid material(s). The continuous-type reactor needs a large amount of investment cost, but is suitable for mass-production. As for the batch-type reactor, a reaction time of 1 minute~8 hours is suitable. If the reaction time is too long, impurities can be easily included and the particles grow and thus it is difficult to make nano particles. If the reaction time is too short, the conversion rate of the reaction is low. As for the continuous-type reactor, a residence time of 1 minute~1 hour is suitable. However, if the residence time is too long, the productivity is low and large particles are obtained, and if the residence time is too short, the conversion rate of the reaction is low. A residence time of 1 minute~20 minutes is more suitable. In case of using a batch-type reactor, the reaction material may be stirred during the reaction, and a stirring rate of 100~1000 rpm is suitable. However, the reaction may be performed without the stirring process, which makes the constitution and operation of the reactor simple and easy for application.

Since the reaction using microwaves is conducted in a very fast rate, it is preferable to enhance the uniformity and solubility of the reaction materials and to irradiate microwaves in a condition pre-treated to partly form crystal nuclei. If the reaction by microwaves is started in a condition that is not pre-treated, the reaction gets slow, or impurities can be easily included, or the uniformity of the particle size can get lower. However, the process itself gets more simple. Pre-treating can be performed by treating the reaction materials with supersonic waves or vigorously stirring. As for said pre-treating temperature, a temperature between room temperature and reaction temperature is preferable. However, it has a disadvantage that if the temperature is too low, the pre-treating effect is weak and if the pre-treating temperature is too high, impurities are easily generated and the pre-treating facility becomes complex. It is suitable that said pre-treating is conducted for 1 minute~5 hours. If treated with supersonic waves, at least 1 minute is suitable, and if treated by stirring, at least 5 minutes is suitable. In case of performing the pre-treating step by stirring, it is preferable to stir the metal component and the organic compound in the presence of a solvent in 50~2,000 rpm for 5~600 minutes, and in case of performing the pre-treating step by irradiating supersonic waves, it is more preferable to irradiate supersonic waves of 15,000 Hz~30 MHz for 1~600 minutes. If the pre-treating time is too short, the pre-treating effect is weak, and if the pre-treating time is too long, the pre-treating efficiency becomes low. Performing the pre-treating using supersonic waves is more preferable in terms of pre-treating time and uniformity of the reaction material.

The second embodiment of the present invention relates to a method for preparing porous organic-inorganic hybrid material(s) comprising the following steps:

(1) preparing a reaction solution containing a mixture of a metal precursor, an organic compound which may act as a ligand and a solvent;

(2) heating the reaction solution; and (3) purifying the porous organic-inorganic hybrid material(s) obtained in the step (2) by treatment with a solvent, a solution wherein an inorganic salt is dissolved or a mixture thereof.

In said preparation method, step (3) can be performed optionally when necessary.

The porous organic-inorganic hybrid material(s) prepared by said preparation method according to the present invention can be obtained as nanoparticles, and the size of said nano particle is about 450 nm or below. Also, the porous organic-inorganic hybrid material(s) prepared by said preparation method according to the present invention can be in a form of powder, thin film, membrane, pellet, ball, foam, slurry, honeycomb, bead, mesh, etc.

The porous organic-inorganic hybrid material(s) in a form of nanoparticles, thin film or membrane can be easily prepared by methods such as electric heating and irradiating microwaves after immersing the substrate to the mixed reaction solution.

The preparation method of the porous organic-inorganic hybrid material(s) of the present invention prepares organic-inorganic hybrid material(s) having nano size particles wherein use of hydrofluoric acid has been eliminated in the hydrothermal synthesis for preparing nanoporous materials. Also, as a purifying method for increasing the surface area of the porous organic-inorganic hybrid material(s), the method is characterized by further comprising a step of purifying impurities within the pore of the organic-inorganic hybrid material(s) by treating them using inorganic salts such as ammonium chloride or potassium fluoride, etc. in addition to the solvent generally used.

Also, the porous organic-inorganic hybrid material(s) has a novel use as an adsorbent. In particular, the adsorbent of the porous organic-inorganic hybrid material(s) according to the present invention can easily perform adsorption and desorption at a temperature of 100° C. and below, and the adsorption amount per weight of the adsorbent is high. Thus, the adsorbent can be used as a water adsorbent that can be applied to humidifiers, dehumidifiers, coolers/heaters, a refrigerating machine, an air conditioner, etc. Further, the porous organic-inorganic hybrid material(s) of the present invention having a large surface area and uniform pore properties can be used as an adsorbent having excellent adsorption efficiency against specific hazardous materials.

In the preparation method of the present invention, as a metal component, which is one of components contained in porous organic-inorganic hybrid material(s), any metal can be used. The representative metal components include Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Mg, Ca, Sr, Ba, Sc, Y, Al, Ga, In, Tl, Si, Ge, Sn, Pb, As, Sb, Bi, etc. In particular, transition metals which easily form coordination compound are suitable. Among said transition metals, chromium, vanadium, iron, nickel, cobalt, copper, titanium and manganese, etc. are suitable, and chromium and iron are the most suitable one. In addition to transition metals, representative elements forming a coordination compound and metals such as lanthanide can also be used. Among elements, aluminum and silicon are suitable, and among lanthanide metals, cerium and lanthanum are suitable. As a metal source, metal itself, and any compound of metal can be used.

In the second embodiment of the present invention, the organic compound which may be another component contained in the organic-inorganic hybrid material(s) and may act as a ligand, and the solvent used in the synthesis of the organic-inorganic hybrid material(s) are the same as those used in the first embodiment.

In order to regulate the crystal growth rate of the nanoporous organic-inorganic hybrid material(s), an acid, in particular, a mixed-acid comprising hydrofluoric acid along with nitric acid, hydrochloric acid and hydrofluoric acid can be used.

Meanwhile, in the process using hydrofluoric acid, there may be a limitation in using reactors other than the Teflon reactor. Until now, for the crystal growth rate of the nanoporous organic-inorganic hybrid material(s), it is well known that the nuclei formation rate is low, while the crystal growth rate is relatively high. Therefore, in reaction materials including hydrofluoric acid, the nuclei formation rate becomes relatively slow due to the strong bonding characteristics between metal ion and fluoride ion, and thus it may be difficult to obtain nanoporous materials having a small crystal size.

Therefore, in another aspect of the present invention, the method for preparing porous organic-inorganic hybrid material(s) of the present invention is characterized by using an inorganic acid except hydrofluoric acid for preparing porous organic-inorganic hybrid material(s), in order to solve the above problems caused by using hydrofluoric acid. Thereby, nanoporous organic-inorganic hybrid material(s) having a relatively small nano particle size can be prepared by said preparation method of the present invention without using hydrofluoric acid at all.

Also, in order to remove the metal or organic ligand present as impurities within the pores of the porous organic-inorganic hybrid material(s) prepared by the second embodiment of the present invention, impurities were conventionally removed using a solvent. However, as for such case, there is a limitation in removing organic or inorganic impurities chelated within the pore. In comparison with the above, in the preparation method of the present invention, impurities within the pore of nanoporous organic-inorganic hybrid material(s) can be efficiently removed by treating porous organic-inorganic hybrid material(s) using an inorganic salt, in particular, comprising monovalent or divalent cation selected from the group consisting of $NH^+_4$, alkali metal and alkali earth metal, and monovalent or divalent anion selected from the group consisting of halogen anion, carbonic acid ion ($CO_3^{2-}$), nitric acid ion and sulfuric acid ion. Accordingly, nanoporous organic-inorganic hybrid material(s) having large surface area can be obtained. At least one inorganic salt selected from the group consisting of a salt comprising $Ca^{2+}$ or $Mg^{2+}$ as divalent cation and $F^-$, $I^-$ or $Br^-$ as monovalent anion, a salt comprising monovalent cation and divalent anion, $NH_4F$, $KF$, $KI$ and $KBr$ can be used as said inorganic salt.

In the present invention, it has been confirmed by measuring the surface area that the nitrogen adsorption amount of the nanoporous organic-inorganic hybrid material(s) after being treated with inorganic salt increases by 200 ml/g.

In addition to the hydrothermal synthetic using the electric heating, hydrothermal synthesis in a batch-type manner or continuous-type manner with irradiating microwaves can be used. Also, the membrane or thin film of the organic-inorganic hybrid material(s) can be prepared by irradiating microwaves to heat after immersing the substrate to the mixed solution of the reaction materials from said step (1). Further, heating the mixed solution may be conducted by conventional method such as steam heating or oil heating, however the heating method is not limited thereto.

In the present invention, the reaction temperature for preparing porous organic-inorganic hybrid material(s) is not substantially limited. However, a temperature of at least room temperature or at least 100° C. is suitable. A temperature of from room temperature to 250° C., or 100~250° C. is preferable, and a temperature of 150~220° C. is more preferable. If said reaction temperature is too low, the reaction rate is slow and thus not efficient, and if the reaction temperature exceeds 250° C. and thus too high, materials having no pores can be easily obtained and the reaction rate becomes too fast so that impurities can be easily included. Also, the inner pressure of the reactor becomes higher, which makes the constitution of the reactor not economic. Although the reactor pressure is not substantially limited, it is convenient to synthesize the materials at autogeneous pressure of the reaction materials at reaction temperature. Also, the reaction may be performed at high pressure by adding inert gas such as nitrogen, helium.

According to the preparation method of the present invention, novel porous organic-inorganic hybrid material(s) represented by formula of $M_3OH(H_2O)_2O[C_6H_4(CO_2)_2]_3$ (M=Fe, Cr, V or Al) or a hydrate thereof, or formula of $M_3O(H_2O)_2OH[C_6H_3—(CO_2)_3]_2$ (M=Fe, Cr, V or Al) or a hydrate thereof which do not contain fluorine, in particular, novel porous organic-inorganic hybrid material(s) represented by formula of $Cr_3OH(H_2O)_2O[C_6H_4(CO_2)_2]_3 \cdot nH_2O$ ($0.1 \leq n \leq 50$) or formula of $Fe_3O(H_2O)_2OH[C_6H_3—(CO_2)_3]_2 \cdot nH_2O$ ($0.1 \leq n \leq 50$) can be obtained.

Also, the porous organic-inorganic hybrid material(s) obtained by the preparation method of the present invention can be used as a catalyst for oxidation reaction or as an acid catalyst.

In addition, the porous organic-inorganic hybrid material(s) prepared according to the preparation method of the present invention can be used as an adsorbent having excellent adsorption and desorption efficiency. In particular, in case of being used as a water adsorbent, since desorption easily occurs at a low temperature of 100° C. and below, a very excellent efficiency can be achieved in humidifiers, dehumidifiers, etc. by using such properties. Further, in case of using the porous organic-inorganic hybrid material(s) prepared according to the preparation method of the present invention as an adsorbent of VOC, a material causing sick house syndrome, specific hazardous materials can be removed efficiently. Further, the porous organic-inorganic hybrid material(s) may be used as an adsorbent for storing, separating and being reacted gases such as $CO_2$, CO, NOx, SOx, $H_2$, $O_2$, $N_2$, methane, paraffin, olefin, hydrocarbon, hydrogen sulfide, ammonia, formaldehyde, amine, or liquids such as gasoline, diesel oil, alcohol, etc.

In particular, in case the porous organic-inorganic hybrid material(s) obtained by the preparation method of the present invention is used as a low-temperature water adsorbent, it can be confirmed that it has a low temperature desorption property of 100° C. and below, preferably 50~100° C., and a very fast water adsorption rate compared with the conventional organic-inorganic nanoporous material(s) containing HF.

The porous organic-inorganic hybrid material(s) may be processed to various shaped bodies such as powder, thin film, membrane, pellet, ball, foam, slurry, honeycomb, bead, mesh, etc. by conventional methods. Organic or inorganic binders may be used for preparing shaped bodies. Examples of inorganic binders may include, but are not limited to, silica, alumina, layer-structured compound, metal alkoxide and metal halide. Examples of organic binders may include, but are not limited to, alcohol, cellulose, polyvinylalcohol and polyacrylate. The content of binder in shaped bodies may be 50% by weight or less based on the total weight of the shaped bodies.

Advantageous Effects

As stated above, the porous organic-inorganic hybrid material(s) containing iron prepared according to the present invention has a large adsorption amount of water and has an excellent desorption amount property at low temperature. Thus, it can be used in dehumidifiers, humidifiers, heaters or coolers as an adsorbent. In particular, it has an advantage that the desorption temperature is very low, and thus the cost for operating such equipments can be remarkably reduced.

Also, in another aspect, although the porous organic-inorganic hybrid material(s) prepared according to the novel preparation method of the present invention do not use hydrofluoric acid during the hydrothermal synthesis, they are nanoporous materials having high crystallinity. In particular, their surface area can be increased by purifying them by removing the impurities within the pore of the nanoporous organic-inorganic hybrid material(s) by treating them with an inorganic salt such as ammonium chloride or potassium fluoride, etc. In addition, the porous organic-inorganic hybrid material(s) prepared according to the preparation method of the present invention can be used as an adsorbent having excellent adsorption and desorption efficiency. In particular, in case of being used as a water adsorbent, desorption easily occurs at a low temperature of 100° C. and below. Thus, using such properties, a very excellent efficiency can be achieved in humidifiers, dehumidifiers, etc. Further, in case of using the porous organic-inorganic hybrid material(s) prepared according to the preparation method of the present invention as an adsorbent of VOC, a material causing sick house syndrome, specific hazardous materials can be removed efficiently.

BRIEF DESCRIPTION OF THE DRAWINGS

FIG. 1 is an X-ray diffraction pattern of iron benzenetricarboxylate organic-inorganic adsorbent obtained by Example 1.

FIG. 2 is an isotherm result of nitrogen adsorption of iron benzenetricarboxylate organic-inorganic adsorbent obtained by Example 1.

FIG. 3 is a graph showing the water adsorption property of the adsorbent using iron benzenetricarboxylate of Examples 1 & 2 and zeolite Y of Comparative Example 1: it is the result of performing desorption of water adsorbent at 70° C. (Examples 1 & 2) or 200° C. (Comparative Example 1), and adsorption at a relative humidity of 68%.

FIG. 4 is a graph showing the water desorption experiment results regarding the adsorbent of Example 1 and Comparative Example 1: Example 1 is the water desorption result at 70° C. and Comparative Example 1 is the water desorption result at 200° C.

FIG. 5 is an X-ray diffraction pattern of the chromium terephthalate, which is a porous organic-inorganic hybrid material(s) prepared in accordance with the preparation method of Example 3 of the present invention.

FIG. 6 is the result of X-ray diffraction patterns before and after purifying the chromium terephthalate which is the porous organic-inorganic hybrid material(s) prepared in accordance with the purifying method of Example 3 of the present invention, wherein (a) is the pattern before purifying, and (b) is the pattern after purifying.

FIG. 7 is an isotherm result of nitrogen adsorption of the chromium terephthalate which is the porous organic-inorganic hybrid material(s) obtained by Example 4 of the present invention.

FIG. 8 is electron microscope images of iron benzenetricarboxylate organic-inorganic hybrid material(s), which is the porous organic-inorganic hybrid material(s) obtained by Example 5 and Comparative Example 4 of the present invention.

FIG. 9 is the result of the water adsorption property of the porous organic-inorganic hybrid material(s) containing iron obtained by Examples 5 & 6 and Comparative Example 4 of the present invention.

DETAILED DESCRIPTION OF THE DRAWINGS

Examples described below are to further explain features and advantages of the subject matter of the present disclosure, but not limited to the examples presented below. The subject matter of the present disclosure should not be limited to the specific embodiments and examples described herein. In light of the present disclosure, a skilled artisan may easily perceive that it is possible to modify, substitute, add and combine a part of the constitutions disclosed in the present disclosure other than various exemplary embodiments and examples.

MODE FOR INVENTION

Example 1

Preparation of Porous Organic-Inorganic Hybrid Material(s) (Fe-BTC) by Microwaves Irradiation After adding metallic iron 1 mmol, 1M $HNO_3$ 60 ml, 5M HF (aqueous solution) 40 ml and 1,3,5-benzenetricarboxylic acid (BTCA) 7 mmol to a Teflon reactor, distilled water was added. The final molar ratio of the reaction material was Fe:HF:HNO$_3$:BTCA:H$_2$O=1:2:0.6:0.7:278. The mixed reaction material was stirred in 500 rpm for 20 minutes at room temperature to make the reaction material as homogeneous as possible. After mounting the Teflon reactor containing said pre-treated reaction material on a microwaves reactor (CEM company, model Mars-5) and then raising the temperature to 200° C. by irradiating microwaves (2.54 GHz), crystallization was performed by maintaining the reaction material at 200° C. for 2 minutes. Then, the reaction material was cooled to room temperature, centrifuged, washed with distilled water and dried to obtain a porous organic-inorganic hybrid material(s) (Fe-BTC). The X-ray diffraction pattern of the solid phase porous organic-inorganic hybrid material(s) obtained as above is as shown in FIG. 1. As a result of elementary analysis, it showed a molar ratio of Fe:C:F=1:6.5:0.32, and as a result of a nitrogen adsorption experiment, it had a BET surface area of 2,050 m$^2$/g and a pore volume of 1.0 ml/g. And it formed as porous particles with yield of 86% (FIG. 2).

The above results show that the material has a crystal structure similar to the Cr-MIL-100 structure, which has been previously published [Bulletin of Korean Chemical Society vol. 26, p. 880 (2005)].

Example 2

Preparation of Porous Organic-Inorganic Hybrid Material(s) (Fe-BTC) by Electric Heating A porous organic-inorganic hybrid material(s) was prepared by the same method as Example 1, except that the organic-inorganic hybrid material(s) was prepared by heating for 144 hours by electric heating using the conventional Convection oven instead of irradiating microwaves as a heat source. As a result of XRD analysis, it can be confirmed that relative intensity of the peak was different; however, a diffusion pattern was shown in the same position as Example 1 as for the crystal structure of the organic-inorganic hybrid material(s) prepared as above. As a result of nitrogen adsorption experiment, it showed a BET surface area of 1,820 m$^2$/g and a pore volume of 0.9 ml/g.

Comparative Example 1

Zeolite Water Adsorbent

Zeolite Y (Aldrich company, Si/Al=5.6, surface area=827 m$^2$/g, pore volume=0.35 ml/g) used as a commercial water adsorbent was prepared.

Comparative Example 2

Preparation of Porous Organic-Inorganic Hybrid Material(s) (Fe-BTC) Using a Single Acid A porous organic-inorganic hybrid material(s) was prepared by the same method as Example 1, except that the hybrid material was prepared using a single acid which is not a nitric acid. After adding metallic iron 1 mmol, 5M HF (aqueous solution) 40 ml and 1,3,5-benzenetricarboxylic acid (BTCA) 7 mmol to a Teflon reactor, distilled water was added. The final molar ratio of the reaction material was Fe:HF:BTCA:H$_2$O=1:2:0.6:278. The temperature of microwave irradiation to the organic-inorganic hybrid material(s) was 200° C., and the reaction was carried out for an hour. The yield of the solid phase porous organic-inorganic hybrid material(s) obtained was 82%. The X-ray diffraction shape of the porous organic-inorganic hybrid material(s) was very similar to the results as in Example 1, but its overall peak strength is low. Also, as a result of a nitrogen adsorption experiment, it showed a BET surface area of 1,590 m$^2$/g and a pore volume of 0.7 ml/g.

Experimental Example 1

Water Adsorption Test

After vacuum drying the adsorbent obtained from Examples 1 & 2 at 70° C. for 30 minutes, a water adsorption test was performed by the gravimetric method (FIG. 3). Even at a relative humidity of 68%, the water adsorption amount per weight of the adsorbent was 0.67 g/g Example 1, and 0.59 g/g in Example 2.

Compared with zeolite Y used as the commercial water adsorbent of Comparative Example 1, as a result of performing the water adsorption test in the same manner after vacuum drying zeolite Y at 200° C. for 30 minutes, the water adsorption amount was 0.35 g/g (FIG. 3). That is, although the desorption temperature of the adsorbent of the example was 70° C., the adsorbent of the present invention showed a water adsorption amount that is at least 1.6 times larger.

Also, the adsorbent of Example 1 prepared by using microwaves showed an adsorption amount of 0.4 g/g after the first 5 minutes, and 0.56 g/g after 10 minutes, whereas the adsorbent of Comparative Example 1 showed an adsorption amount of 0.25 g/g after 5 minutes, and 0.28 g/g after 10 minutes. Thus, it can be known that the adsorbent according to Example 1 of the present invention has a very high initial adsorption rate.

Experimental Example 2

Water Desorption Test

After the adsorbent prepared in Example 1 and sodium zeolite Y (NaY) were put at the upper layer of the in a desiccator carrying the saturated solution of ammonium chloride and maintained for 3 days to sufficiently adsorb water, the desorption amount was analyzed by the gravimetric method. As for the desorption condition, the weight reduction of the adsorbent was measured while flowing out 300 ml/min of nitrogen. The desorption temperature of the adsorbent of Example 1 was 70° C., and the desorption temperature of sodium zeolite Y (NaY) of Comparative Example 1 was 200° C.

FIG. 4 is a graph illustrating the result of weight reduction according to the progress of time by having the total weight of the adsorbent adsorbing water as 100%. The fact that the weight reduction rate does not decrease any more means that all of the water that can be desorbed has been desorbed. Referring to the result of Example 1, after 10 minutes, it showed a weight reduction of about 40% by weight. As for Comparative Example 1, it showed a weight reduction of about 25% by weight. As for Example 1, the water adsorption amount that can be desorbed per weight of the adsorbent was 40/60=0.67 g/g, and as for Comparative Example 1, the water adsorption amount that can be desorbed per weight of the adsorbent was 25/75=0.33 g/g. Therefore, it can be known that the absolute water adsorption amount of the adsorbent of Example 1 is at least 2 times faster than that of the adsorbent of Comparative Example 1. Also, the desorption rate of the first 5 minutes is higher in the adsorbent of Example 1 than the adsorbent of Comparative Example 1.

From the above results, it can be known that the adsorbent according to the present invention can easily desorb water at a temperature of 100° C., and that it has a high water adsorption amount per unit weight. Using such properties, the adsorbent is applied to humidifiers and dehumidifiers and is expected to present an excellent efficiency in adjusting humidity.

Example 3

Cr-BDC-1

After adding $Cr(NO_3)_3 \cdot 9H_2O$, and 1,4-benzenedicarboxylic acid (BDCA) to a Teflon reactor, distilled water was added so that the final molar ratio of the reaction material was $Cr:HNO_3:BDCA:H_2O=1:0.1:1:272$. Basically, if $Cr(NO_3)_3$ dissolves in water, it is hydrated to become a strong acid. Thus, it has the same effect as adding $HNO_3$. After putting the Teflon reactor containing said reaction material in an electric oven and reacting it for 11 hours at 210° C., it was cooled to room temperature, centrifuged, washed with distilled water and dried to obtain chromium terephthalate (Cr-BDC) as a porous organic-inorganic hybrid material(s). The result of the X-ray diffraction analysis of the thus prepared Cr-BDC showed characteristic diffraction peaks of $2\theta$ values at about 3.3, 5.2, 5.9, 8.5 and 9.1, and it can be known that the chromium terephthalate having cubic crystallinity was obtained (FIG. 5). It has been confirmed that the XRD pattern of the chromium terephthalate crystal obtained from the present example was consistent with the values published in prior art [Science 23, 2040, 2005]. Thus, it can be shown that the porous organic-inorganic hybrid material(s) can be obtained very efficiently by an environmental friendly process that does not use hydrofluoric acid (HF) in the reaction materials. As a result of ICP analysis, it can be shown that the chromium terephthalate, which is a porous organic-inorganic hybrid material(s) obtained, does not contain F, and thus its structure is the same as MIL-101 but it does not include F in its structure, thus being materials that can be represented by formula of $Cr_3OH(H_2O)_2O[C_6H_4(CO_2)_2]_3 \cdot nH_2O$ (n~25).

Example 4

Cr-BDC-2

Organic-inorganic hybrid material(s) with improved surface area were prepared by removing impurities such as 1,4-benzenedicarboxylic acid and chromium oxide, etc. which does not bind within the crystalline structure present in pores of the porous materials by putting the porous organic-inorganic hybrid material(s) 1 g prepared in Example 3 in 50 ml of 1M $NH_4F$ and stirring it at 70° C. From the X-ray diffraction pattern (FIG. 6), it can be confirmed that its crystallinity was maintained without being damaged after treating with ammonium fluoride. Also, from the result of measuring the nitrogen adsorption of the porous organic-inorganic hybrid material(s) before and after treating with ammonium fluoride, it can be shown that organic-inorganic hybrid material(s) having features such that the surface area increases by 700 $m^2/g$ (before treating with ammonium fluoride, 3,373 $m^2/g \rightarrow$ after treatment, 4,074 $m^2/g$) due to the ammonium fluoride treatment, and the adsorption amount at $P/P_o=0.5$ increases by 200 ml/g (before treating with ammonium fluoride, 1,050 ml/g $\rightarrow$ after treatment, 1,250 ml/g) can be obtained (FIG. 7).

Example 5

Preparation of Porous Organic-Inorganic Hybrid Material(s) (Fe-BTC-1) by Microwaves Irradiation After adding metallic iron 1 mmol, 1M $HNO_3$ 60 ml and 1,3,5-benzenetricarboxylic acid (BTCA) 7 mmol to a Teflon reactor, distilled water was added. The final molar ratio of the reaction material was $Fe:HNO_3:BTCA:H_2O=1:0.6:0.7:278$. The reaction material was stirred in 500 rpm for 20 minutes at room temperature, to make reaction material homogeneous. After mounting the Teflon reactor containing said pre-treated reaction material on a microwaves reactor (CEM company, model Mars-5) and raising the temperature to 200° C. by irradiating microwaves (2.54 GHz), crystallization was performed by maintaining the reaction mixture at 200° C. for 2 minutes. Then, the reaction mixture was cooled to room temperature, centrifuged, washed with distilled water and dried to obtain the porous organic-inorganic hybrid material(s) (Fe-BTC). It is shown that the shape of the X-ray diffraction pattern was similar to that of the Cr-MIL-100 structure which is the crystal structure previously published [Bulletin of Korean Chemical Society vol. 26, p. 880 (2005)]. As a result of ICP analysis, it can be known that the chromium terephthalate, which is a porous organic-inorganic hybrid material(s) obtained, does not contain F, and thus its structure is the same as MIL-100, but it does not include F within its structure, and it is a material that can be represented by formula of $Fe_3O(H_2O)_2OH[C_6H_3-(CO_2)_3]_2 \cdot nH_2O$ (n~14.5). As a result of the nitrogen adsorption test, it has been confirmed that the surface area of the porous organic-inorganic hybrid material(s) (Fe-BTC) was at least 1,700 $m^2/g$. As a result of the analysis of electron microscope, it can be known that the particle size became very small to 200~500 nm and below (FIG. 8a).

Example 6

Preparation of Porous Organic-Inorganic Hybrid Material(s) (Fe-BTC-2) by Electric Heating A porous organic-inorganic hybrid material(s) was prepared in the same method as Example 3 except that the organic-inorganic hybrid material(s) was prepared by heating for 6 hours by an electric heating using the conventional electric heating instead of irradiating microwaves as a heat source. As a result of XRD analysis, it can be confirmed that relative intensity of the peak was different; however, a diffraction pattern was shown in the same position as Example 3 as for the crystal structure of the organic-inorganic hybrid material(s) prepared as above. As a result of analysis using an electron microscope, a relatively large crystal whose particle size is 1 μm was obtained.

Example 7

Cr-BDC-3

An organic-inorganic hybrid material(s) was prepared in the same method as Example 3 except that heating by microwaves irradiation was used instead of the electric heating in Example 3. However, the organic-inorganic hybrid material(s) was prepared by using microwaves reaction device of 2.5 GHz and maintaining the reaction temperature at 210° C. for 40 minutes. The X-ray diffraction pattern analysis showed that this material has the same structure as in Example 3.

Example 8

Fe-BDC-3

An organic-inorganic hybrid material(s) was prepared in the same manner as in Example 3 except that Fe was used instead of $Cr(NO_3)_3 \cdot 9H_2O$. Also, pure porous organic-inorganic hybrid material(s) was prepared using the post-treating step of Example 4. It can be known from the X-ray diffraction pattern that the material having the same structure as in Example 3 was obtained.

Example 9

V-BDC-1

An organic-inorganic hybrid material(s) was prepared in the same manner as in the post-treating step of Examples 3 & 4 except that $VCl_3$ was used instead of $Cr(NO_3)_3 \cdot 9H_2O$ as in Example 8. The X-ray diffraction pattern shows that the material having the same structure as in Example 3 was obtained. The electron microscope photograph shows that the organic-inorganic hybrid material(s) having uniform particle size of 50-80 nm was obtained.

Example 10

After vacuum drying 0.1 g of the organic-inorganic hybrid material, Fe-BTC respectively obtained from Examples 5 & 6 and Comparative Example 4 at 150° C. for 30 minutes, the adsorption test of water was performed by the gravimetric method (FIG. 9). At a relative humidity of 60%, the water adsorption amount per weight of the adsorbent within the first 5 minutes was measured to be 0.36 g/g in Example 5, and 0.34 g/g in Example 6. This shows a result improved respectively by 24%, 17% than the adsorption amount of Comparative Example 4, 0.29 g/g. In particular, it has been confirmed that the water adsorption rate of the entire region from the initial stage of adsorption to 5 minutes is very high. As such, in case of using the porous organic-inorganic hybrid material(s) according to the present invention as a low-temperature water adsorbent, it can be known that the adsorbent can easily desorb at a temperature of 100° C. and below, and using such property, it can achieve a very excellent efficiency in humidifiers, dehumidifiers, etc.

Example 11

As a result of performing an adsorption test for an hour by adding benzene 1 g, which is the volatile organic compound, to the porous organic-inorganic hybrid material(s) Cr-BDC 1 g obtained by the method of Example 3, it has been confirmed that 0.73 g benzene is removed by adsorption. It has been confirmed that such value is an adsorption amount that is 3.5 times larger than 0.19 g benzene, which is the adsorption amount of the same amount of active carbon of Darco (surface area 1,600 $m^2/g$).

Comparative Example 3

Cr-BDC-4

A nanoporous organic-inorganic hybrid material(s) was prepared using hydrofluoric acid for preparing a reaction mixture in the preparation method as in Example 3. The final molar ratio of the reaction mixture was $Cr:HF:BDCA:H_2O=1:1:1:272$. A result of analyzing the surface area of the nanoporous organic-inorganic hybrid material(s) prepared as above shows that the organic-inorganic hybrid material(s) has adsorption amount of 1044 ml/g and BET surface area of 3,439 $m^2/g$ at $P/Po=0.5$.

Comparative Example 4

Fe-BTC

A nanoporous organic-inorganic hybrid material(s) was prepared using hydrofluoric acid for preparing a reaction mixture in the preparation method as in Example 5. The final molar ratio of the reaction mixture was $Fe:HF:HNO_3:BTCA:H_2O=1:1:0.6:0.7:278$. As a result of X-ray diffraction analysis of the organic-inorganic hybrid material(s) prepared as above, it can be known that the material having very large crystal size (1~5 μm) was obtained instead of a organic-inorganic hybrid material(s) having the same crystallinity as in Example 5 (FIG. 8b).

From the results of the examples and comparative examples above, in comparison with the method using hydrofluoric acid, it has been confirmed that nanoporous organic-inorganic hybrid material(s) having the same crystallinity were prepared by the preparation method of the present invention that does not use hydrofluoric acid. In particular, it has been confirmed that the surface area increases by at least 10% when treated with inorganic salt such as ammonium salt and potassium fluoride, etc. Also, it has been confirmed that the nanoporous organic-inorganic hybrid material(s) prepared according to the preparation method of the present invention have very high activity as a catalyst. In addition, the porous organic-inorganic hybrid material(s) prepared according to the preparation method of the present invention can be used as an adsorbent having excellent adsorption and desorption efficiency. In particular, when used as a water adsorbent, since desorption occurs easily at a low temperature of 100° C. and below, a very excellent efficiency as a humidifier, dehumidifier, etc. can be achieved using such properties. Further, in case of using the porous organic-inorganic hybrid material(s) prepared according to the preparation method of the present invention as an adsorbent of specific hazardous materials such as VOC, a material causing sick house syndrome, the specific hazardous materials in vapor phase and particulate phase can be removed efficiently.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed:

1. A water adsorbent comprising porous organic-inorganic hybrid material(s), wherein the porous organic-inorganic hybrid material(s) contains iron and is prepared by a method comprising:
   (a) preparing a reaction solution containing a mixture of an iron or iron salt as an iron precursor, an organic ligand, a solvent and a mixed-acid comprising nitric acid and hydrofluoric acid as a reaction accelerant; and
   (b) heating the reaction solution.

2. The water adsorbent of claim 1, wherein the porous organic-inorganic hybrid material(s) is selected from the group consisting of iron terephthalate and iron benzenetricarboxylate.

3. The water adsorbent of claim 1, wherein an amount of the water adsorption in the porous organic-inorganic hybrid material(s) containing iron is 0.2~2.0 g per gram of the porous organic-inorganic hybrid material(s).

4. The water adsorbent of claim 1, wherein the reaction solution is heated at the temperature of from room temperature to 250° C.

5. The water adsorbent of claim 1, wherein a batch-type reactor or a continuous-type reactor is used for the preparation.

6. The water adsorbent of claim 1, wherein the method further comprises pre-treating the reaction solution after the step (a) by stirring or by irradiating with supersonic waves to form crystal nuclei.

7. An adsorbent comprising porous organic-inorganic hybrid material(s) prepared by a method comprising:
(a) preparing a reaction solution containing a mixture of a metal precursor, an organic compound which may act as a ligand, and a solvent;
(b) heating the reaction solution; and
(c) purifying the porous organic-inorganic hybrid material(s) obtained in the step (b) by treatment with a solvent, a solution wherein an inorganic salt is dissolved or a mixture thereof.

8. The adsorbent of claim 7, wherein the reaction solution further contains an acid.

9. The adsorbent of claim 7, wherein the acid is an inorganic acid except for hydrofluoric acid.

10. The adsorbent of claim 7, wherein the reaction solution is heated at the temperature of from room temperature to 250° C.

11. The adsorbent of claim 7, wherein the inorganic salt used in the step (c) comprises a monovalent or divalent cation selected from the group consisting of ammonium, alkali metals and alkali earth metals, and a monovalent or divalent anion selected from the group consisting of halogen anions, carbonate anion ($CO_3^{2-}$), nitrate ion and sulfate ion, and impurities in the obtained porous organic-inorganic hybrid material(s) is purified by treatment with said inorganic salt.

12. The adsorbent of claim 7, wherein the metal precursor is at least one metal or compound thereof selected from the group consisting of Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Mg, Ca, Sr, Ba, Sc, Y, Al, Ga, In, Tl, Si, Ge, Sn, Pb, As, Sb and Bi.

13. The adsorbent of claim 12, wherein the metal precursor is at least one metal or compound thereof selected from the group consisting of Al, Fe, V, Mn, Mg and Cr.

14. The adsorbent of claim 7, wherein the organic compound which may act as a ligand is a compound containing at least one functional group selected from the group consisting of carboxylic acid group, anion group of carboxylic acid, amino group ($-NH_2$), imino group

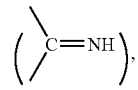

amide group, sulfonic acid group ($-SO_3H$), anion group of sulfonic acid ($-SO_3^-$), methanedithioic acid group ($-CS_2H$), anion group of methanedithioic acid ($-CS_2^-$), pyridine group and pyrazine group, or a mixture thereof.

15. The adsorbent of claim 14, wherein the compound containing carboxylic acid is derived from a compound selected from the group consisting of benzenedicarboxylic acid, naphthalenedicarboxylic acid, benzenetricarboxylic acid, naphthalenetricarboxylic acid, pyridinedicarboxylic acid, bipyridyldicarboxylic acid, formic acid, oxalic acid, malonic acid, succinic acid, glutaric acid, hexanedioic acid, heptanedioic acid and cyclohexyldicarboxylic acid.

16. The adsorbent of claim 7, wherein the porous organic-inorganic hybrid material(s) is chromium terephthalate, iron terephthalate, aluminum terephthalate or vanadium terephthalate.

17. The adsorbent of claim 7, wherein the porous organic-inorganic hybrid material(s) is iron benzenetricarboxylate, chromium benzenedicarboxylate, aluminum benzenetricarboxylate, or vanadium benzentricarboxylate.

18. The adsorbent of claim 7, wherein the porous organic-inorganic hybrid material(s) are prepared in a form of nanoparticles.

19. The adsorbent of claim 7, wherein the porous organic-inorganic hybrid material(s) are prepared in a form of thin film, membrane, pellet, ball, foam slurry, honeycomb, bead or mesh.

20. The adsorbent of claim 7, wherein the porous organic-inorganic hybrid material(s) does not contain fluorine and is represented by a formula of $M_3OH(H_2O)_2O[C_6H_4(CO_2)_2]_3$ (M=Fe, Cr, V or Al) or a hydrate thereof.

21. The adsorbent of claim 7, wherein the porous organic-inorganic hybrid material(s) does not contain fluorine and is represented by formula of $M_3O(H_2O)_2OH[C_6H_3-(CO_2)_3]_2$ (M=Fe, Cr, V or Al) or a hydrate thereof.

22. A water adsorbent wherein water is adsorbed by using the adsorbent according to claim 7.

23. The water adsorbent of claim 22, used for water adsorption in a dehumidifier, a humidifier, coolers, heaters, a refrigerating machine or an air conditioner.

24. The adsorbent of claim 7, used for adsorbing specific hazardous materials in vapor phase or particulate phase.

25. The adsorbent of claim 7, used for adsorbing volatile organic compounds in vapor phase or particulate phase.

26. The adsorbent of claim 7, used for adsorbing one or more materials in vapor phase or particulate phase selected from the group consisting of formaldehyde, acetaldehyde, tar, nitrosoamines and polycyclicaromatic hydrocarbons, causing a sick house syndrome.

27. The adsorbent of claim 7, used for adsorbing one or more gases selected from $CO_2$, CO, NOx, SOx, or $H_2$.

* * * * *